United States Patent
Bingley et al.

(10) Patent No.: US 11,806,188 B2
(45) Date of Patent: Nov. 7, 2023

(54) SYSTEM AND METHOD FOR DETERMINING HEMODYNAMIC PARAMETERS OF A PATIENT

(71) Applicant: KONINKLIJKE PHILIPS N.V., Eindhoven (NL)

(72) Inventors: Peter Bingley, Mierlo (NL); Balasundar Iyyavu Raju, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 435 days.

(21) Appl. No.: 16/308,087

(22) PCT Filed: Jun. 15, 2017

(86) PCT No.: PCT/EP2017/064727
§ 371 (c)(1),
(2) Date: Dec. 7, 2018

(87) PCT Pub. No.: WO2017/216322
PCT Pub. Date: Dec. 21, 2017

(65) Prior Publication Data
US 2019/0298303 A1 Oct. 3, 2019

Related U.S. Application Data

(60) Provisional application No. 62/351,450, filed on Jun. 17, 2016.

(51) Int. Cl.
*A61B 8/08* (2006.01)
*A61B 8/06* (2006.01)
(Continued)

(52) U.S. Cl.
CPC ............ *A61B 8/0883* (2013.01); *A61B 8/065* (2013.01); *A61B 8/12* (2013.01); *A61B 8/4494* (2013.01);
(Continued)

(58) Field of Classification Search
CPC ......... A61B 8/0883; A61B 8/065; A61B 8/12; A61B 8/4494; A61B 8/463; A61B 8/5223; A61B 8/54; A61B 8/4488; G16H 50/30
See application file for complete search history.

(56) References Cited

U.S. PATENT DOCUMENTS 5,976,088 A * 11/1999 Urbano ............... G01S 7/52066
600/443
6,679,849 B2 * 1/2004 Miller .................. A61B 5/6819
600/463
(Continued)

FOREIGN PATENT DOCUMENTS

WO 9219157 A1 11/1992
WO 2014097014 A1 6/2014

OTHER PUBLICATIONS

Theodosios Saranteas et al. Transesophageal echocardiography and vascular ultrasound in the diagnosis of catheter-related persistent left superior vena cava thrombosis, European Journal of Echocardiography, vol. 10, Issue 3, May 2009, pp. 452-455 (Year: 2009).*

(Continued)

*Primary Examiner* — Joel Lamprecht
*Assistant Examiner* — Ashish S Jasani (57) ABSTRACT

This disclosure describes a system that determines hemodynamic parameters of a patient. The system may include a transesophageal echocardiogram (TEE) probe including an ultrasound transducer comprising a matrix array of piezoelectric elements, the transesophageal echocardiogram
(Continued)

(TEE) probe configured to obtain a plurality of clinically relevant views of the patient's heart from a single position. The system may include one or more processors, operatively connected to the TEE probe. The one or more processors are configured by machine-readable instructions to control the TEE probe by electronically steering an ultrasound beam provided by the ultrasound transducer to obtain the plurality of clinically relevant views of the patient's heart; receive the plurality of clinically relevant views of the patient's heart provided by the TEE probe; and determine one or more physiological parameters of the patient's heart based on the received plurality of clinically relevant views of the patient's heart.

17 Claims, 6 Drawing Sheets (51) Int. Cl.
    *A61B 8/12*     (2006.01)
    *A61B 8/00*     (2006.01)

(52) U.S. Cl.
    CPC ............ *A61B 8/463* (2013.01); *A61B 8/5223* (2013.01); *A61B 8/54* (2013.01); *A61B 8/4488* (2013.01)

(56) References Cited

U.S. PATENT DOCUMENTS

| | | | |
|---|---|---|---|
| 8,303,505 B2 | 11/2012 | Webler et al. | |
| 8,641,627 B2 | 2/2014 | Roth et al. | |
| 10,078,893 B2 | 9/2018 | Guterman | |
| 2003/0045795 A1* | 3/2003 | Bjaerum | G01S 7/52034 600/441 |
| 2005/0131302 A1* | 6/2005 | Poland | G01S 15/8927 600/459 |
| 2010/0152590 A1 | 6/2010 | Moore et al. | |
| 2010/0174194 A1* | 7/2010 | Chiang | A61B 8/4483 600/447 |
| 2010/0210945 A1* | 8/2010 | Zhang | A61B 6/466 600/509 |
| 2011/0054322 A1 | 3/2011 | Zanatta | |
| 2011/0263983 A1* | 10/2011 | Peszynski | A61B 1/0052 600/443 |
| 2013/0278776 A1 | 10/2013 | Guterman et al. | |
| 2013/0310691 A1 | 11/2013 | Furman | |
| 2014/0046188 A1* | 2/2014 | Yen | A61B 8/4236 600/444 |
| 2014/0171798 A1* | 6/2014 | Tobias | G01S 7/52085 600/437 |
| 2016/0038121 A1 | 2/2016 | Waechter-Stehle et al. | |
| 2016/0310110 A1* | 10/2016 | Dodd | A61B 8/54 |
| 2017/0252013 A1* | 9/2017 | Choi | A61B 8/46 |
| 2019/0029639 A1* | 1/2019 | Gifford, III | A61B 8/12 |

OTHER PUBLICATIONS

Guo, Zirong, and Huaxin Zeng. "Simulation and analysis of weighted fair queuing algorithms in OPNET." 2009 International Conference on Computer Modeling and Simulation. IEEE, 2009.*

Howard, et al., "hTEE measured SVC index: A useful tool for predicting fluid responsiveness in the trauma patient", Mercier University School of Medicine, 1 page (Absract).

* cited by examiner

SYSTEM AND METHOD FOR DETERMINING HEMODYNAMIC PARAMETERS OF A PATIENT

CROSS-REFERENCE TO PRIOR APPLICATIONS

This application is the U.S. National Phase application under 35 U.S.C. § 371 of International Application No. PCT/EP2017/064727, filed on Jun. 15, 2017, which claims the benefit of U.S. Provisional Application No. 62/351,450, filed Jun. 17, 2016. These applications are hereby incorporated by reference herein, for all purposes.

BACKGROUND

1. Field

The present disclosure relates to a system and method for capturing image data and determining hemodynamic parameters of a patient.

2. Description of the Related Art

Critical patients in an intensive care unit have their physiological functions monitored via hemodynamic parameters related to the heart and circulation. For unstable patients, continuous monitoring of hemodynamic parameters such as cardiac output (CO), stroke volume (SV) and ejection fraction (EF) is conducted. In addition, for treating hemodynamically unstable patients, fluid status is monitored, which can be determined based on superior vena cava diameter (SVC) variations, as administering fluid may help the patient to recover, while administering too much fluid may be detrimental for the patient.

SUMMARY

Accordingly, one or more aspects of the present disclosure relate to a system configured to determine hemodynamic parameters of a patient. The system comprises a transesophageal echocardiogram (TEE) probe including an ultrasound transducer comprising a matrix array of piezoelectric elements and one or more processors operatively connected to the transesophageal echocardiogram (TEE) probe and/or other components. The transesophageal echocardiogram (TEE) probe is configured to obtain a plurality of clinically relevant views of the patient's heart from a single position. The one or more processors are configured by machine-readable instructions to control the transesophageal echocardiogram (TEE) probe by electronically steering an ultrasound beam provided by the ultrasound transducer to obtain the plurality of clinically relevant views of the patient's heart; receive the plurality of clinically relevant views of the patient's heart provided by the transesophageal echocardiogram (TEE) probe; and determine one or more physiological parameters of the patient's heart based on the received plurality of clinically relevant views of the patient's heart.

Another aspect of the present disclosure relates to a method for determining hemodynamic parameters of a patient with a system. The system comprises a transesophageal echocardiogram (TEE) probe including an ultrasound transducer comprising a matrix array of piezoelectric elements, the transesophageal echocardiogram (TEE) probe configured to obtain a plurality of clinically relevant views of the patient's heart from a single position and one or more processors, operatively connected to the transesophageal echocardiogram (TEE) probe, the one or more processors configured by machine-readable instructions. The method comprises controlling, by the one or more processors, the transesophageal echocardiogram (TEE) probe by electronically steering an ultrasound beam provided by the ultrasound transducer to obtain the plurality of clinically relevant views of the patient's heart; receiving, by the one or more processors, the plurality of clinically relevant views of the patient's heart provided by the transesophageal echocardiogram (TEE) probe; and determining, by the one or more processors, one or more physiological parameters of the patient's heart based on the received plurality of clinically relevant views of the patient's heart.

Still another aspect of present disclosure relates to a system for determining hemodynamic parameters of a patient. The system comprises means for obtaining a plurality of clinically relevant views of the patient's heart from a single position; means for controlling the means for obtaining the plurality of clinically relevant views of the patient's heart, the means for controlling including means for electronically steering an ultrasound beam provided by the means for obtaining the plurality of clinically relevant views of the patient's heart to obtain the plurality of clinically relevant views of the patient's heart; means for receiving the plurality of clinically relevant views of the patient's heart provided by the means for obtaining the plurality of clinically relevant views of the patient's heart; and means for determining one or more physiological parameters of the patient's heart based on the received plurality of clinically relevant views of the patient's heart.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
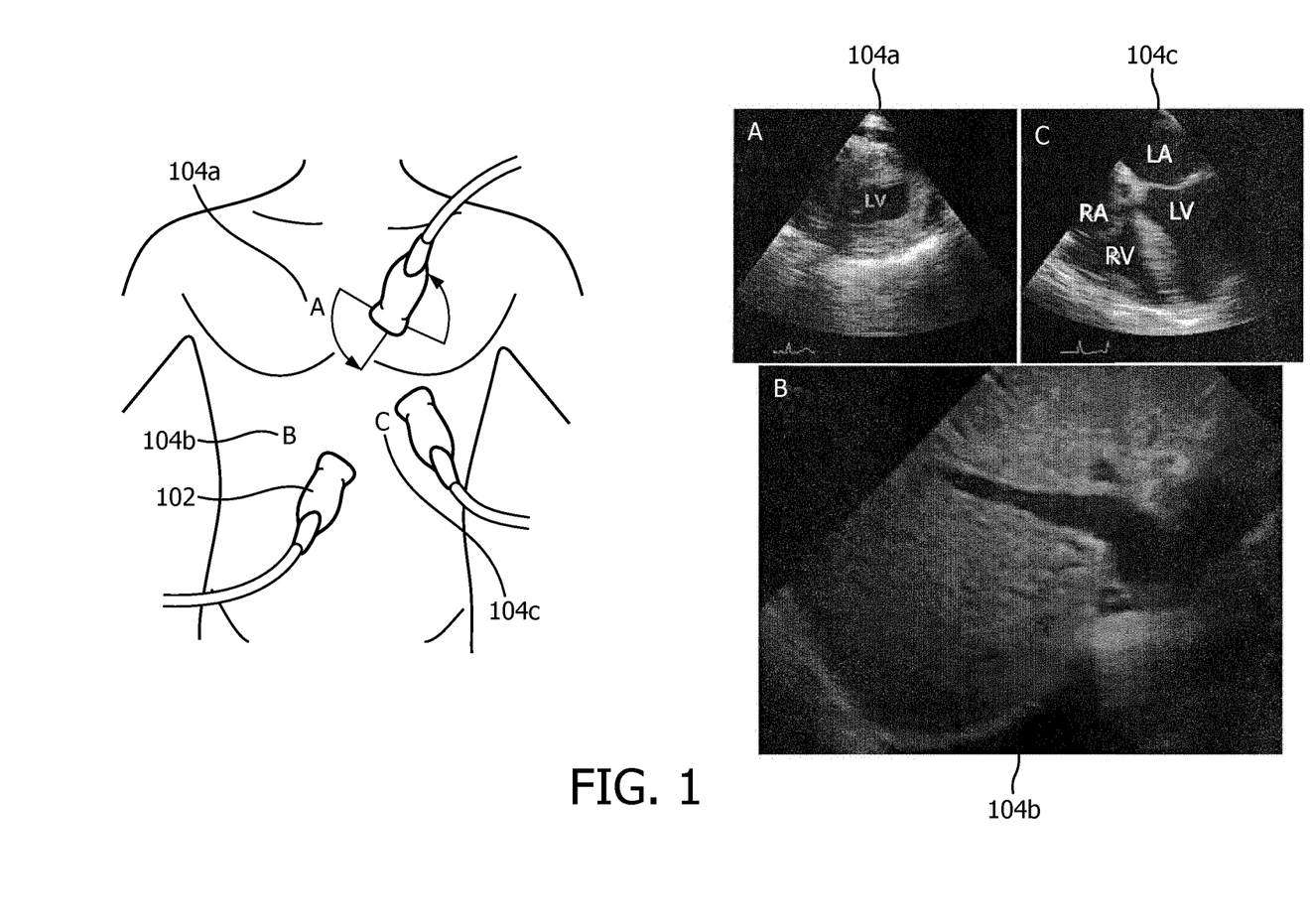
FIG. 1 illustrates locations of transthoracic echocardiography (TTE) probes during a TTE procedure and corresponding views of the heart.

FIG. 1 illustrates locations of transthoracic echocardiography (TTE) probes during a TTE procedure and corresponding views of the heart. Transthoracic echocardiography (TTE) is a noninvasive imaging procedure for quantitative and qualitative evaluation of cardiac anatomy and function. During a TTE procedure, the heart may be imaged from multiple viewing angles 104a, 104b, 104c, etc. by placing a TTE transducer 102 directly on the patient's chest in four windows: parasternal 104a, apical 104c, subcostal 104b, and suprasternal (not shown). TTE offers superior resolution of the anterior structures, such as the right ventricle, right ventricular outflow tract, pulmonic valve, and anterior pericardium. TTE apical views provide superior imaging of the pericardium and left ventricular apex. However, due to use of lower ultrasound frequencies (3-5 MHz) to achieve greater depth penetration by the ultrasound, spatial resolution may be degraded. Due to the non-invasive nature of TTE, ultrasound waves have to pass through skin, muscle, and/or bone tissue. Therefore, being overweight or having certain lung diseases can interfere with images of the heart when the transducer is placed on the chest wall.

Figure 2:
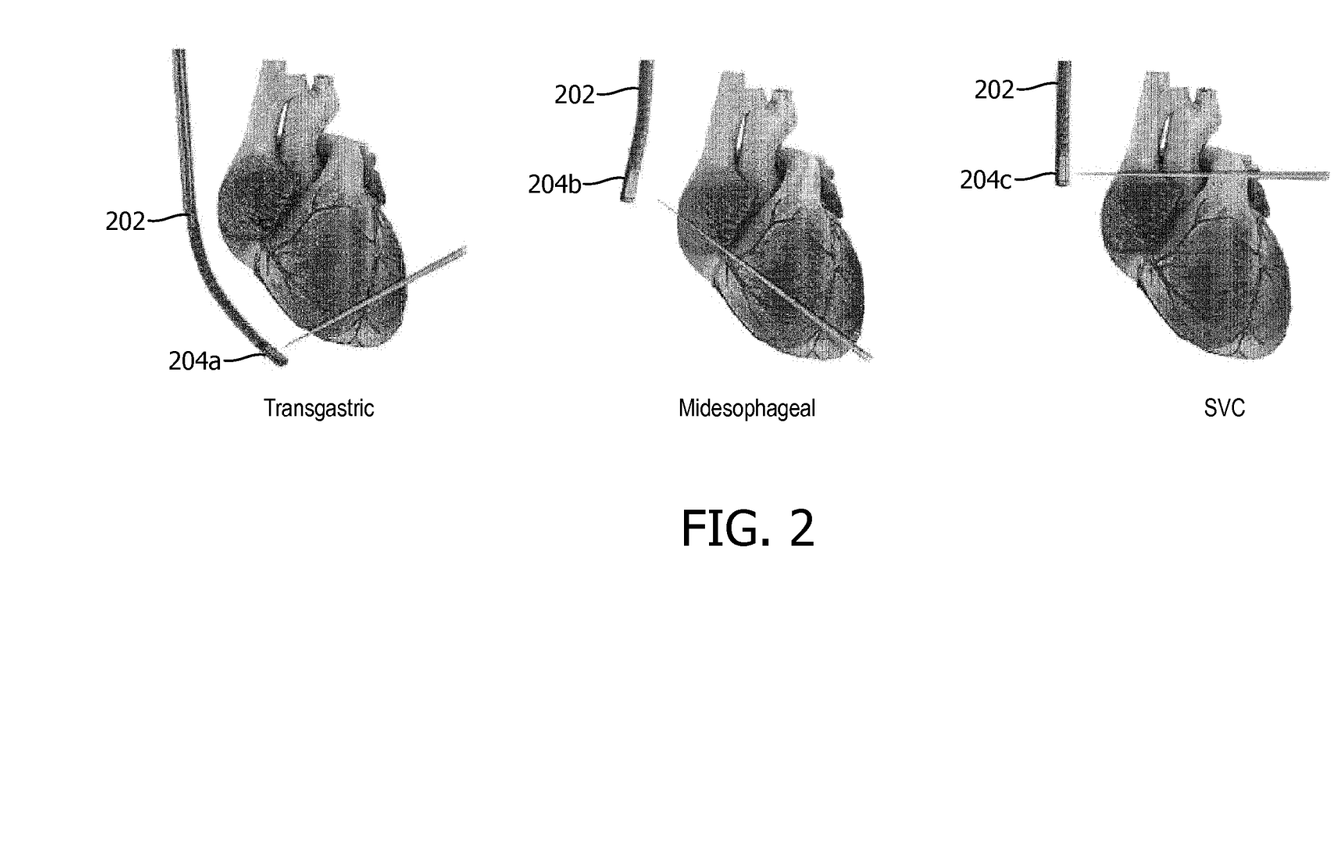
FIG. 2 illustrates locations of transesophageal echocardiograph (TEE) probes during a TEE procedure.

Imaging of the posterior structures, such as the left atrium, mitral valve and subvalvular apparatus, interatrial septum and left atrial appendage is best achieved with a Transesophageal echocardiogram (TEE). FIG. 2 illustrates locations of transesophageal echocardiograph (TEE) probes during a TEE procedure. During a Transesophageal echocardiogram (TEE) procedure, a flexible ultrasound gastroscope 202 (e.g. an ultrasound transducer attached to an end of an endoscope) is advanced along the esophagus (tube connecting the throat with stomach) and into the stomach to image the heart. Due to the nature of the TEE procedure and the TEE probe's close proximity to the heart, less depth penetration by the ultrasound wave is required. Therefore, the transducer may utilize higher frequencies (5-7 MHz) to provide superior spatial resolution of posterior cardiac structures. A TEE probe may include a bending neck assembly, which allows the probe to bend in order to acquire desired images or views or to navigate in curved passages. Typically, as illustrated in FIG. 2, the TEE probe is required to be in one position 204a to obtain the Transgastric view of the heart, in another position 204b to obtain the Midesophageal view of the heart and yet in another position 204c for obtaining the SVC view of the heart.

Current solutions for measuring hemodynamic parameters are either very invasive requiring multiple arterial lines (e.g. Swan-Ganz, PiCCO), do not provide continuous measurements (e.g. PiCCO, transthoracic ultrasound), or are not accurate for unstable patients (e.g. Finapres, ClearSight). In addition, transthoracic (TTE) ultrasound does not work reliably for obese patients. Furthermore, commonly used TEE probes (e.g., probes provided by ImaCor) do not support continuous monitoring as the probes need to be moved manually to different positions in the esophagus in order to obtain the views needed for determining the hemodynamic parameters. For example, if a probe were manually cycled through positions, the "same" view would be captured from slightly different positions every time, which would introduce an appreciable variance between each successive measurement of the same parameter.

Figure 3:
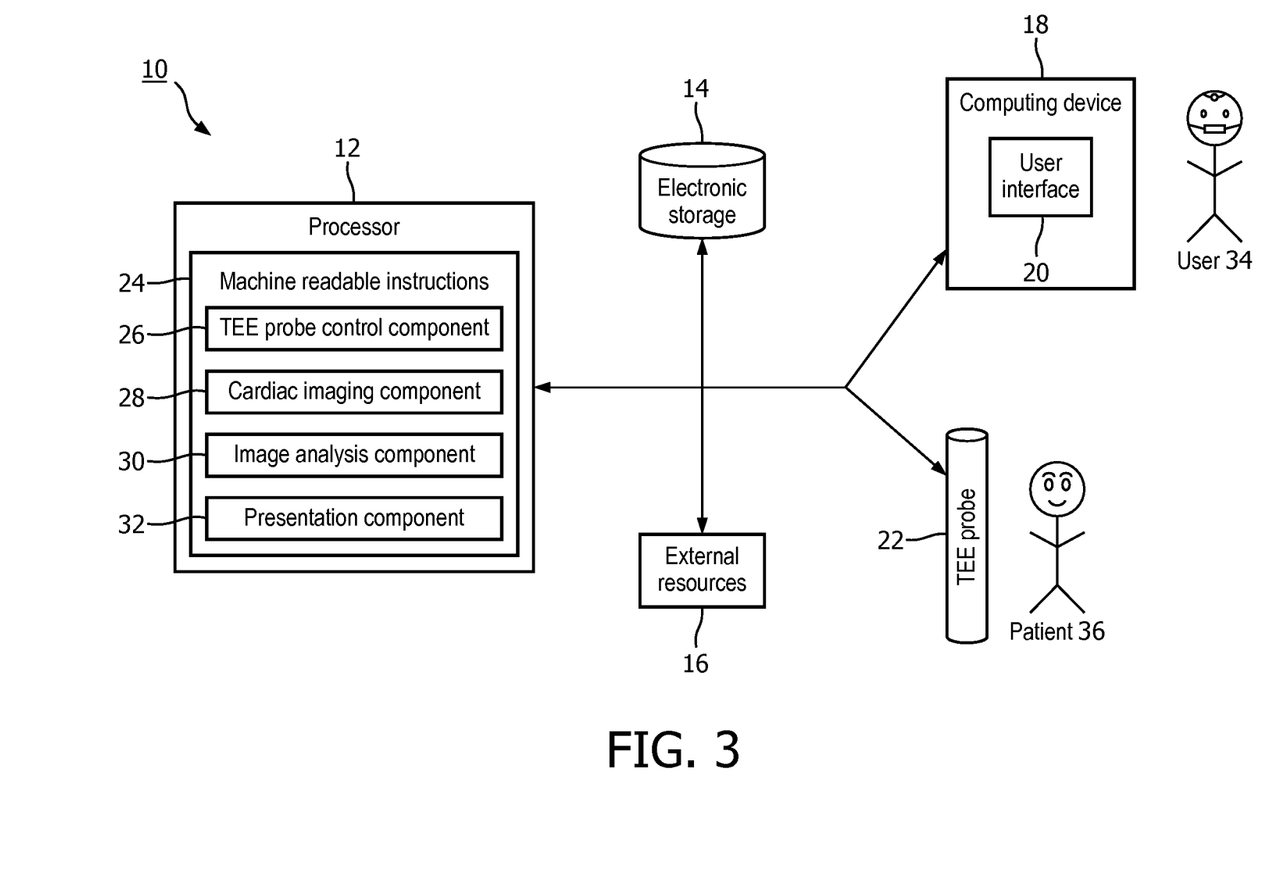
FIG. 3 illustrates a schematic illustration of a system configured to determine hemodynamic parameters of a patient.

FIG. 3 is a schematic illustration of a system 10 configured to determine hemodynamic parameters of a patient 36. System 10 facilitates monitoring hemodynamic parameters of patient 36 from multiple views of patient 36's heart obtained with a TEE probe without the need for repositioning the probe, thereby enabling continuous monitoring of the hemodynamic parameters.

System 10 is configured to facilitate hemodynamic monitoring of patient 36 for a prolonged amount of time without the need for a user 34 intervention and/or repositioning of the probe. Hemodynamic monitoring of patient 36 may include measuring different hemodynamic parameters substantially continuously using a transesophageal echocardiogram (TEE) probe 22. The transesophageal echocardiogram (TEE) probe 22 used for such monitoring may include means for electronically steering an ultrasound beam emitted by individual piezoelectric transducers disposed on the TEE probe such that a plurality of clinically relevant view of patient 36's heart may be obtained. Different physiological parameters may be derived from the plurality of relevant views of patient 36's heart by analyzing the plurality of relevant views of patient 36's heart using image analysis algorithms. In some embodiments, system 10 includes one or more of a processor 12, electronic storage 14, external resources 16, a computing device 18, a TEE probe 22, and/or other components.

The transesophageal echocardiogram (TEE) probe 22 may be formed with two-dimensional transducer arrays including a plurality of acoustic elements arranged in a matrix configuration. Matrix arrays may facilitate three-dimensional steering of the ultrasonic beam such that utilizing a single transducer may be sufficient for inspection at variable angles. Moreover, matrix arrays may facilitate faster inspection of objects and/or organs with complex geometries. The acoustic elements may include piezoelectric crystals that can transmit/receive waves independently at different times. Responsive to an electric drive signal, the acoustic elements may mechanically deform, thereby creating acoustic waves (e.g. ultrasound waves) propagating from the transducer to the medium (e.g. patient 36's heart). Upon encountering different interfaces with differing acoustic indexes in the medium, echoes of the waves may be created and propagated back (e.g. reflected) toward individual elements of the transducer array. Responsive to the receipt of the reflected waves, individual elements of the transducer may deform, thereby creating an electric signal that may be processed, transformed into digital images, and/or analyzed for determining physiological parameters. By adjusting a time delay of the electric drive signal and/or electric signal corresponding to the received reflected waves on individual elements of the transducer array, the ultrasound beam emitted from the transducer array may be electronically steered and/or focused. For example, time delays may be applied to the elements to create constructive interference of the wave fronts resulting in steering of the ultrasonic beam. In some embodiments, the transesophageal echocardiogram (TEE) probe is stationary in a single position while obtaining a plurality of clinically relevant views of patient 36's heart. In some embodiments, a plurality of clinically relevant views of patient 36's heart is obtained during an imaging session by the TEE probe 22. The imaging session begins when the transesophageal echocardiogram (TEE) probe 22 is inserted into patient 36's esophagus and the imaging session ends when the transesophageal echocardiogram (TEE) probe 22 is removed from patient 36's esophagus. In some embodiments, the transesophageal echocardiogram (TEE) probe 22 is stationary in a single position during the imaging session (e.g. without the need for repositioning the probe during the imaging session).

Processor 12 is configured to provide information processing capabilities in system 10. As such, processor 12 may comprise one or more of a digital processor, an analog processor, a digital circuit designed to process information, an analog circuit designed to process information, a state machine, and/or other mechanisms for electronically processing information. Although processor 12 is shown in FIG. 3 as a single entity, this is for illustrative purposes only. In some embodiments, processor 12 may comprise a plurality of processing units. These processing units may be physically located within the same device (e.g., a server), or processor 12 may represent processing functionality of a plurality of devices operating in coordination (e.g., a server, computing device 18 associated with user 34, devices that are part of external resources 16, and/or other devices.)

As shown in FIG. 3, processor 12 is configured via machine-readable instructions 24 to execute one or more computer program components. Such instructions 24 may be stored in a non-transitory storage medium such as a L1/L2/etc. cache, in system memory, or in a storage device. As used herein, the term "non-transitory machine-readable storage medium" will be understood to encompass both volatile memory (e.g., SRAM and DRAM) and nonvolatile memory (e.g., flash memory, magnetic memory, and optical memory), but to exclude transitory signals per se. The one or more computer program components may comprise one or more of a TEE probe control component 26, a cardiac imaging component 28, an image analysis component 30, a presentation component 32, and/or other components. Processor 12 may be configured to execute components 26, 28, 30, and/or 32 by software; hardware; firmware; some combination of software, hardware, and/or firmware; and/or other mechanisms for configuring processing capabilities on processor 12.

It should be appreciated that although components 26, 28, 30, and 32 are illustrated in FIG. 3 as being co-located within a single processing unit, in embodiments in which processor 12 comprises multiple processing units, one or more of components 26, 28, 30, and/or 32 may be located remotely from the other components. The description of the functionality provided by the different components 26, 28, 30, and/or 32 described below is for illustrative purposes, and is not intended to be limiting, as any of components 26, 28, 30, and/or 32 may provide more or less functionality than is described. For example, one or more of components 26, 28, 30, and/or 32 may be eliminated, and some or all of its functionality may be provided by other components 26, 28, 30, and/or 32. As another example, processor 12 may be configured to execute one or more additional components that may perform some or all of the functionality attributed below to one of components 26, 28, 30, and/or 32.

Figure 4:
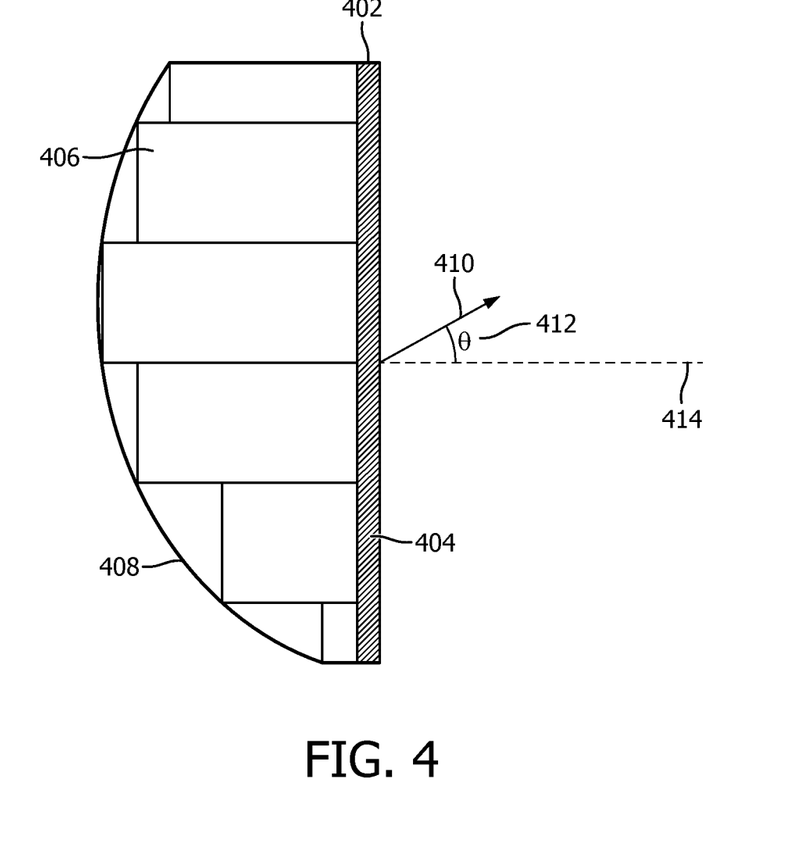
FIG. 4 illustrates electronic beam steering of an ultrasound transducer according to one or more embodiments.

TEE probe control component 26 is configured to control the transesophageal echocardiogram (TEE) probe by electronically steering the ultrasound beam provided by the ultrasound transducer to obtain the plurality of clinically relevant views of patient 36's heart. Electronic control of the TEE probe by electronically steering the ultrasound beam facilitates obtaining the plurality of clinically relevant views of patient 36's heart without physically bending and/or repositioning of the TEE probe. Such control may be facilitated by providing a time delay for drive signals corresponding to individual elements of the transducer array. The TEE probe control component 26 may adjust drive signal time delays with respect to one another to create a path of maximum acoustic power propagation in the medium. The resultant propagated wave may represent a summation of individual waves transmitted by transmitting elements (e.g. acoustic contributions of the elements chosen for transmission). Responsive to receipt of the reflected wave, the TEE probe control component 26 may time adjust individual signals created by corresponding elements such that varying angles of transmission (steered beams) are accounted for. By way of a non-limiting example, FIG. 4 illustrates electronic beam steering of an ultrasound transducer according to one or more embodiments. As illustrated in FIG. 4, different delays 406 are applied to signals transmitted by individual elements 404 in the array 402. In this example an asymmetrical curved delay profile 408 is applied to individual elements 404 of the array 402 to deflect the resultant beam 410 from a horizontal axis 414 at an angle 412. The delay profile 408 may be obtained by using known time delay circuits. These time delays cause the beam to constructively interfere at a specific depth and direction. To create a plane of image, the delay profiles may be adjusted to steer the beam in successively different directions within the image plane. The use of a matrix array provides flexibility in selection of arbitrary image planes within a 3D volume.

Figure 5:
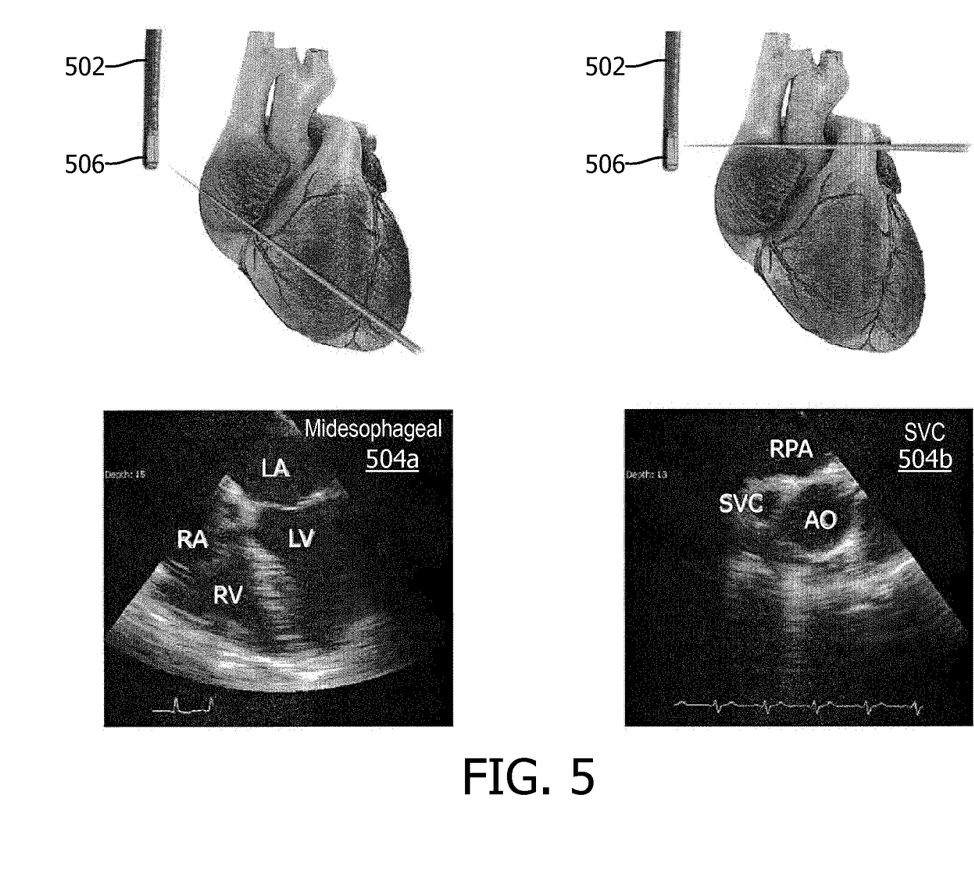
FIG. 5 illustrates a transesophageal echocardiograph (TEE) procedure with electronic beam steering according to one or more embodiments.

Returning to FIG. 3, cardiac imaging component 28 is configured to receive the plurality of clinically relevant views of patient 36's heart provided by the transesophageal echocardiogram (TEE) probe 22. In some embodiments, cardiac imaging component 28 may be configured to facilitate switching between the plurality of clinically relevant views of patient 36's heart in a time-multiplexed manner. In some embodiments, the cardiac imaging component 28 may facilitate adjusting a frame-rate update of the plurality of clinically relevant views of patient 36's heart such that changes in hemodynamic status of patient 36 are detected. For example, a first view on the left ventricle of patient 36's heart may need to be updated at a high frame rate such that wall motion changes are detected. A second view for the superior vena cava (SVC) imaging may require a lower frame rate as long as the respiratory variation in diameter is detected. The frame-rate update for different views may be selected a priori in a look-up table. In some embodiments, user 34 may select a frame-rate update by utilizing a dial included in user interface 20. The frame-rate update may also be adjusted using information from the measured physiological parameters. For example if one parameter is changing more rapidly, then cardiac imaging component 28 may adjust the frame-rate update by increasing the frame-rate update of the view that provides that parameter. By way of a non-limiting example, FIG. 5 illustrates a transesophageal echocardiograph (TEE) procedure with electronic beam steering according to one or more embodiments. As illustrated in FIG. 5, by using electronic beam steering, two clinically relevant views (left view 504a: Midesophageal, right view 504b: SVC) may be obtained from the same position 506 of the TEE probe 502 (e.g., TEE probe is in a straightened position near the aorta/superior vena cava of the heart for both the Midesophageal and SVC views).

Returning to FIG. 3, image analysis component 30 is configured to determine one or more physiological parameters of patient 36's heart based on the received plurality of clinically relevant views of patient 36's heart. In some embodiments, image analysis component 30 may be configured such that determining the one or more physiological parameters of patient 36 comprises analyzing the plurality of clinically relevant views of patient 36's heart to extract hemodynamic parameters including one or more of cardiac output (CO), stroke volume (SV), ejection fraction (EF), superior vena cava (SVC) diameter variations, and/or other parameters. In some embodiments, image analysis 30 may utilize algorithms to determine the hemodynamic parameters from the received plurality of clinically relevant views of patient 36's heart. In some embodiments, algorithms may include an automatic boundary extraction algorithm, configured to delineate boundaries of cardiac chambers such that one or more hemodynamic parameters may be derived, and regional wall motion algorithm configured to determine abnormal heart wall motion. The boundaries of the cardiac chambers may be determined using a model based segmentation approach, wherein a heart model may be used to fit the chambers of the heart. Other parameters that could be used include intensity levels and speckle patterns. In some embodiments, image analysis component 30 may be configured to determine a fluid status of patient 36 (e.g. whether patient 36 is properly hydrated). The fluid status of patient 36 may also be monitored, as administering fluid may help patient 36 to recover, while administering too much fluid may be detrimental for patient 36. Image analysis component 30, by analyzing diameter variations (e.g. vein pulsating) in the superior vena cava (SVC), may determine the fluid status of patient 36. For example, if patient 36 is dehydrated and/or lost a substantial amount of blood, diameter variations of the SVC may represent abnormal and very frequent pulsations of the SVC, and if patient 36 is overhydrated, diameter variations of the SVC may represent very insubstantial and infrequent pulsations of the SVC (e.g. SVC may be very rigid).

In some embodiments, presentation component 32 is configured to effectuate presentation of images corresponding to the plurality of clinically relevant views of patient 36's heart on a display provided by computing device 18. Effectuating presentation comprises causing the GUI (as described below) to display one or more views (as described below) with one or more fields (as described below) that convey information related to one or more of the determined parameters, images corresponding to the plurality of clinically relevant views of patient 36's heart, and/or other information to user 34. In some embodiments, presentation component 32 is configured to effectuate presentation of the determined physiological parameters on the display provided by computing device 18. By way of a non-limiting example, FIG. 5 illustrates echocardiogram images corresponding to midesophageal view 504a and SVC view 504b of the heart. In some embodiments, heart chambers, vein, arteries, and/or other cardiac anatomies may be labeled (e.g. in the midesophageal view 504a Right Atrium (RA), Right Ventricle (RV), Left Atrium (LA), and Left Ventricle (LV) are labeled and in the SVC view 504b Right Pulmonary Artery (RPA), Superior Vena Cava (SVC), and Aorta (AO) are labeled). In some embodiments, view illustrated by FIG. 5 may include a heat beat field that visually illustrates cardiac cycles (e.g. heart beats). In some embodiments, FIG. 5 view may include one or more parameter fields configured to display one or more of the determined hemodynamic parameters. In some embodiments, the one or more determined hemodynamic parameters may be displayed in one parameter field. In some embodiments, user 34 may select individual determined hemodynamic parameters to be displayed on the one or more parameter fields.

Returning to FIG. 3, electronic storage 14 comprises electronic storage media that electronically stores information. The electronic storage media of electronic storage 14 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., computing device 18, processor 16, etc.). In some embodiments, electronic storage 14 may be located in a server together with processor 12, in a server that is part of external resources 16, in computing device 18 associated with user 34, and/or other users, and/or in other locations. Electronic storage 14 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 14 may store software algorithms, information determined by processor 12, information received via computing device 18 and/or other external computing systems, information received from external resources 16, and/or other information that enables system 10 to function as described herein. By way of a non-limiting example, electronic storage 14 may store images corresponding to the plurality of clinically relevant views of patient 36's heart and/or other information.

External resources 16 include sources of information (e.g., databases, websites, etc.), external entities participating with system 10 (e.g., a medical records system of a health care provider that stores previous hemodynamic parameter measurements, diagnosis, symptoms, etc. for patient 36), one or more servers outside of system 10, a network (e.g., the internet), electronic storage, equipment related to Wi-Fi technology, equipment related to Bluetooth® technology, data entry devices, computing devices associated with individual users, and/or other resources. For example, in some embodiments, external resources 16 may include the database where the medical records including medical conditions, symptoms, and/or other information relating to patient 36 are stored, and/or other sources of information. In some implementations, some or all of the functionality attributed herein to external resources 16 may be provided by resources included in system 10. External resources 16 may be configured to communicate with processor 12, computing device 18, electronic storage 14, and/or other components of system 10 via wired and/or wireless connections, via a network (e.g., a local area network and/or the internet), via cellular technology, via Wi-Fi technology, and/or via other resources.

Computing device 18 is configured to provide an interface between user 34, and/or other users and system 10. Computing device 18 is configured to provide information to and/or receive information from the user 34, and/or other users. For example, computing device 18 is configured to present a user interface 20 to user 34 to facilitate control, by a user 34, of an effective duty cycle of time spent in each of the plurality of clinically relevant views of patient 36's heart. In some embodiments, user interface 20 includes a plurality of separate interfaces associated with computing device 18, processor 12 and/or other components of system 10.

In some embodiments, computing device 18 is configured to provide user interface 20, processing capabilities, databases, and/or electronic storage to system 10. As such, computing device 18 may include processor 12, electronic storage 14, external resources 16, and/or other components of system 10. In some embodiments, computing device 18 is connected to a network (e.g., the internet). In some embodiments, computing device 18 does not include processor 12, electronic storage 14, external resources 16, and/or other components of system 10, but instead communicate with these components via the network. The connection to the network may be wireless or wired. For example, processor 12 may be located in a remote server and may wirelessly cause display of user interface 20 to user 34 on computing device 18. In some embodiments, computing device 18 is a laptop, a personal computer, a smartphone, a tablet computer, and/or other computing devices. The present disclosure also contemplates that computing device 18 includes a removable storage interface. In this example, information may be loaded into computing device 18 from removable storage (e.g., a smart card, a flash drive, a removable disk) that enables the user 34, and/or other users to customize the implementation of computing device 18. Other exemplary input devices and techniques adapted for use with computing device 18 include, but are not limited to, an RS-232 port, RF link, an IR link, a modem (telephone, cable, etc.) and/or other devices.

User input devices suitable for inclusion in user interface 20 include a touch screen, a keypad, touch sensitive and/or physical buttons, switches, a keyboard, knobs, dials, levers, a display, a graphical user interface (GUI), speakers, a microphone, an indicator light, an audible alarm, a printer, and/or other interface devices. User interface 20 is configured to provide information to and/or receive information from user 34, and/or other users. In some embodiments, the display presents a graphical user interface (GUI) comprising one or more views with one or more fields that convey information related to one or more of the determined parameters, images corresponding to the plurality of clinically relevant views of patient 36's heart, and/or other information to user 34.

Figure 6:
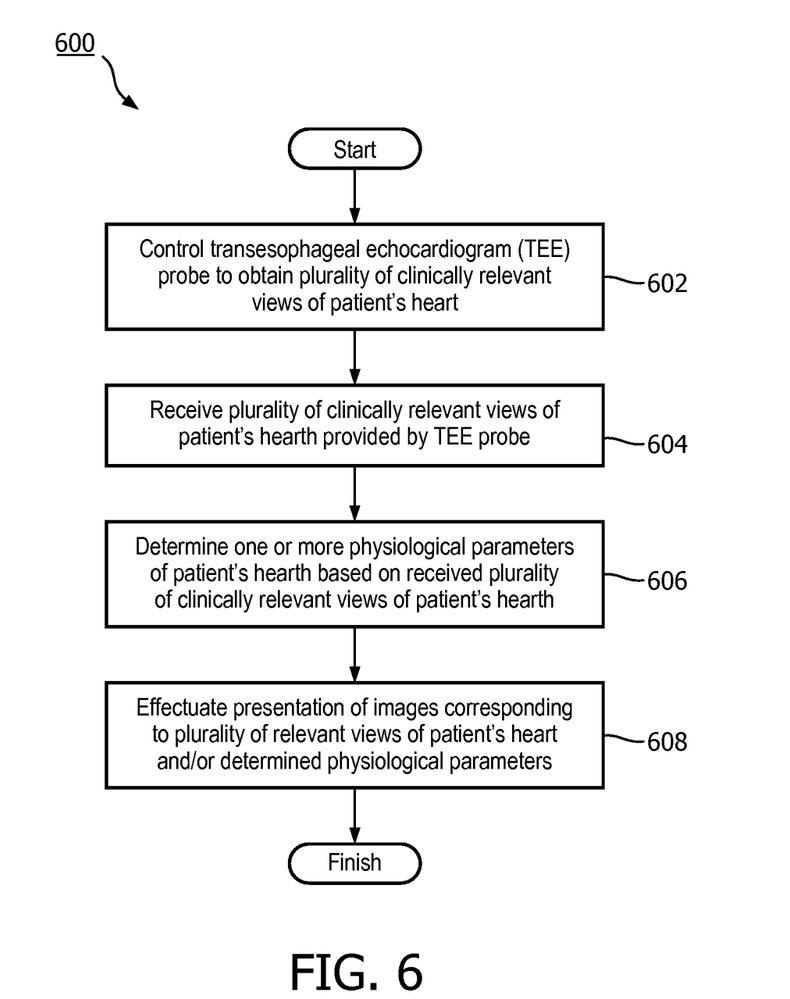
FIG. 6 illustrates a method for determining hemodynamic parameters of a patient.

FIG. 6 illustrates a method 600 for determining hemodynamic parameters of a patient with a system. The system comprises a transesophageal echocardiogram (TEE) probe including an ultrasound transducer including a matrix array of piezoelectric elements and one or more processors operatively connected to the transesophageal echocardiogram (TEE) probe and/or other components. The transesophageal echocardiogram (TEE) probe is configured to obtain a plurality of clinically relevant views of the patient's heart from a single position. The one or more hardware processors are configured by machine readable instructions to execute computer program components. The computer program components comprise a TEE probe control component, a cardiac imaging component, an image analysis component, a presentation component, and/or other components. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, the transesophageal echocardiogram (TEE) probe is controlled by the one or more processors. In some embodiments, controlling the transesophageal echocardiogram (TEE) probe includes electronically steering an ultrasound beam provided by the ultrasound transducer to obtain the plurality of clinically relevant views of the patient's heart. In some embodiments, the transesophageal echocardiogram (TEE) probe is stationary in a single position while obtaining the plurality of clinically relevant views of the patient's heart. In some embodiments, the plurality of clinically relevant views of the patient's heart is obtained during an imaging session. In some embodiments, the imaging session begins when the transesophageal echocardiogram (TEE) probe is inserted into the patient's esophagus and the imaging session ends when the transesophageal echocardiogram (TEE) probe is removed from the patient's esophagus. In some embodiments, the transesophageal echocardiogram (TEE) probe is stationary in the single position during the imaging session. In some embodiments, control, by a user, of an effective duty cycle of time spent in each of the plurality of clinically relevant views of the patient's heart is facilitated by a user interface. In some embodiments, operation 602 is performed by a processor component the same as or similar to TEE probe control component 26 (shown in FIG. 3 and described herein).

In some embodiments, the processor may steer the beam or otherwise control the TEE probe to cycle through a plurality of views and provide real-time, animated image data of each view. For example, where the TEE probe is to capture three different views, the processor may steer the beam to the first view, capture the image, steer to the second view, capture the image, steer to the third view, capture the image, and repeat this sequence indefinitely, until imaging is to stop. These three streams of images may then be shown in sequence to display three animated views and derive parameters therefrom. Such an approach may be easily adapted to a different number of views and would be beneficial, for example, where each view can be acquired at the same frame rate. A more complex scheduling algorithm may be used where different frame rates are desired for each view. For example, where the first view should be captured at twice the frame rate of the second and third views, the processor may steer the probe to capture the first view, second view, the first view, the third view, and then to repeat indefinitely. If the set of views to be monitored or the frame-rates thereof change during operation (e.g., as described above), the scheduling algorithm may be re-executed to determine the new order for steering the beam. Various scheduling algorithms may be employed such as, for example, weighted round robin or weighted fair queueing. In some embodiments, the set frame rates may represent minimum acceptable frame-rates rather than discrete targets. As such, some chosen scheduling algorithms may provide animations at frame-rates higher than the set frame-rate when processor or time resources allow.

At an operation 604, the plurality of clinically relevant views of the patient's heart, provided by the transesophageal echocardiogram (TEE) probe, is received by the one or more processors. In some embodiments, receiving the plurality of clinically relevant views of the patient's heart includes switching, by the one or more processors, between the plurality of clinically relevant views of the patient's heart and adjusting, by the one or more processors, a frame-rate update of the plurality of clinically relevant views of the patient's heart such that changes in hemodynamic status of the patient are detected. In some embodiments, operation 604 is performed by a processor component the same as or similar to cardiac imaging component 28 (shown in FIG. 3 and described herein).

At an operation 606, one or more physiological parameters of the patient's heart are determined based on the received plurality of clinically relevant views of the patient's heart. In some embodiments, determining the one or more physiological parameters of the patient's heart includes analyzing the plurality of clinically relevant views of the patient's heart to extract hemodynamic parameters including one or more of cardiac output (CO), stroke volume (SV), ejection fraction (EF), or superior vena cava (SVC) diameter variations. In some embodiments, operation 606 is performed by a processor component the same as or similar to image analysis component 30 (shown in FIG. 3 and described herein).

At an operation 608, images corresponding to the plurality of clinically relevant views of the patient's heart and/or the determined physiological parameters are presented on a display. In some embodiments, operation 608 is performed by a processor component the same as or similar to presentation component 32 (shown in FIG. 3 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system including a transesophageal echocardiogram (TEE) probe and configured for continuous monitoring of hemodynamic parameters () of a patient without repositioning the TEE probe, the system comprising:
   an ultrasound transducer located in the probe and comprising a matrix array of piezoelectric elements, the ultrasound transducer configured to obtain a plurality of views, including a first view and a second view, of the patient's heart from a single position; and
   one or more processors, operatively connected to the TEE probe, the one or more processors configured by machine-readable instructions to:
   control the TEE probe to switch between the first view and the second view to interleave the acquisition of frames of the first view with frames of the second view in a manner that updates a first frame rate of the first view, the first frame rate being different from a second frame rate of the second view;
   determine a new order for the interleaved acquisition of the frames of the first view and the frames of the second view, wherein the new order is determined using a scheduling algorithm and responsive, at least in part, to the updated first frame rate; and
   determine, in real-time, a first hemodynamic parameter of the patient's heart using data obtained by the ultrasound transducer in the first view and a second hemodynamic parameter of the patient's heart using data obtained by the ultrasound transducer in the second view, wherein the first frame rate is selected based, at least in part, on the first hemodynamic parameter and the second frame rate is selected based, at least in part, on the second hemodynamic parameter.

2. The system of claim 1, wherein the determining of at least one of the first and second physiological parameters of the patient's heart comprises analyzing the respective one of the first and second of views of the patient's heart to extract a respective hemodynamic parameter selected from cardiac output (CO), stroke volume (SV), ejection fraction (EF), and superior vena cava (SVC) diameter variations.

3. The system of claim 1, wherein the one or more processors are further configured by machine-readable instructions to:
   effectuate presentation of images corresponding to the plurality of views of the patient's heart on a display; and/or
   effectuate presentation of the determined physiological parameters on the display.

4. The system of claim 1, further comprising a user interface configured to facilitate control, by a user, of an effective duty cycle of time spent in each of the plurality of views of the patient's heart.

5. The system of claim 1, wherein the processor is configured to provide real-time, animated image data of each of the plurality of views of the patient's heart.

6. The system of claim 1, wherein the plurality of views of the patient's heart comprise a Midesophageal view and a superior vena cava view.

7. The system of claim 1, wherein the first frame rate and the second frame rate are determined based, at least in part, on a weighted round robin scheduling algorithm or a weighted fair queuing scheduling algorithm.

8. The system of claim 1, wherein the ultrasound transducer is configured to achieve the continuous monitoring by obtaining the plurality of views in a single imaging session, the single imaging session beginning when the TEE probe is placed in an esophagus of the patient and the single imaging session ending when the TEE probe is removed from the patient's esophagus, the TEE probe remaining stationary during the single imaging session.

9. A method for continuous monitoring of hemodynamic parameters of a patient, the method comprising:
providing a transesophageal echocardiogram (TEE) probe including an ultrasound transducer comprising a matrix array of piezoelectric elements and configured to acquire a plurality of views of the patient's heart, including a first view and a second view, through electronic beam steering without repositioning the TEE probe;
controlling the TEE probe, by one or more processors communicatively coupled to the TEE probe, to switch between the first view and the second view thereby interleaving the acquisition of frames of the first view with frames of the second view in a manner that updates a first frame rate of the first view, the first frame rate being different from a second frame rate of the second view;
determining, by the one or more processors, a new order for the interleaved acquisition of the frames of the first view and the frames of the second view, wherein the new order is determined using a scheduling algorithm and responsive, at least in part, to the updated first frame rate; and
determining in real-time, by the one or more processors, a first hemodynamic parameter using data acquired by the TEE probe in the first view and a second hemodynamic parameter using data acquired by the TEE probe in the second view, wherein the first frame rate is selected based, at least in part, on the first hemodynamic parameter and the second frame rate is selected based, at least in part, on the second hemodynamic parameter.

10. The method of claim 9, wherein at least one of the first hemodynamic parameter and the second hemodynamic parameter is selected from cardiac output (CO), stroke volume (SV), ejection fraction (EF), and superior vena cava (SVC) diameter variations.

11. The method of claim 10, further comprising determining a fluid status of the patient based on the SVC diameter variations.

12. The method of claim 9 further comprising:
effectuating, by the one or more processors, presentation of images corresponding to the plurality of views of the patient's heart on a display; and/or effectuating, by the one or more processors, presentation of the determined physiological parameters on the display.

13. The method of claim 9, wherein the system further comprises a user interface, and wherein the method further comprises facilitating, by the user interface, control, by a user, of an effective duty cycle of time spent in each of the plurality of views of the patient's heart.

14. A system for continuous monitoring of hemodynamic parameters of a patient, the system comprising:
means for obtaining a plurality of views, including a first view and a second view, of the patient's heart from a single position;
means for controlling the means for obtaining the plurality of views of the patient's heart, the means for controlling including means for switching between the first view and the second view to interleave the acquisition of frames of the first view with frames of the second view in a manner that updates a first frame rate of the first view, the first frame rate being different from a second frame rate of the second view, wherein a new order is determined for the interleaved acquisition of the frames of the first view and the frames of the second view using a scheduling algorithm and responsive, at least in part, to the updated first frame rate; and
means for determining in real-time a first hemodynamic parameter of the patient's heart using data obtained by the means for obtaining the plurality of views, the data being obtained in the first view, and determining a second hemodynamic parameter of the patient's heart using data obtained by the means for obtaining the plurality of views, the data being obtained in the second view, wherein the first frame rate is selected based, at least in part, on the first hemodynamic parameter and the second frame rate is based, at least in part, on the second hemodynamic parameter.

15. The system of claim 14, wherein the means for determining the first and second physiological parameters of the patient's heart comprises means for analyzing the first and second views of the patient's heart to extract hemodynamic parameters including one or more of cardiac output (CO), stroke volume (SV), ejection fraction (EF), or superior vena cava (SVC) diameter variations.

16. The system of claim 14 further comprising:
means for effectuating presentation of images corresponding to the plurality of views of the patient's heart on a display; and/or
means for effectuating presentation of the determined physiological parameters on the display.

17. The system of claim 14 further comprising means for facilitating control, by a user, of an effective duty cycle of time spent in each of the plurality of views of the patient's heart.

* * * * *